United States Patent [19]

Vosburgh

[11] 3,958,569

[45] May 25, 1976

[54] KNEE PROTECTOR AND BRACE

[76] Inventor: Arthur E. Vosburgh, 1245 Brown Road, Ellwood City, Pa. 16117

[22] Filed: May 19, 1975

[21] Appl. No.: 578,386

[52] U.S. Cl. ................................... 128/80 C; 2/22
[51] Int. Cl.² ............................................ A61F 3/00
[58] Field of Search.............. 128/80 C, 80 F, 80 R, 128/80 E, 88, 87, 83, 165; 3/22–27; 2/22–24

[56] References Cited
UNITED STATES PATENTS

| 876,017 | 1/1908 | Roberts | 3/26 |
| 2,770,811 | 11/1956 | Steeper | 3/22 |
| 3,055,359 | 9/1962 | Palmer | 128/80 F |
| 3,194,233 | 7/1965 | Peckham | 128/80 C |
| 3,350,719 | 11/1967 | McClure, Jr. | 128/80 R |
| 3,732,861 | 5/1973 | Lehneis | 128/80 E |
| 3,826,251 | 7/1974 | Ross | 128/80 F |

*Primary Examiner*—John D. Yasko
*Attorney, Agent, or Firm*—Harvey C. Nienow

[57] ABSTRACT

A device to be worn by a person such as an athlete to protect the knee from external objects and to afford strength for the knee joint.

It comprises a thigh member and a calf member as well as a pair of arms extending from each of such members toward the knee joint and on opposite sides of the knee. Each adjacent pair of arms is connected together by a hub member which extends through an opening in one arm and is fastened to the other arm. A washer is mounted between the arms and is formed with an abutment to be engaged by a limit-stop on one of the arms.

The thigh and calf members each comprises a pliable member as well as a flexible cellular material. The cellular material is provided with a tab which extends through a slot in the pliable material such that as the pliable material is firmly attached to the wearer, the tabs can be pulled to straighten the cellular material against the leg. This prevents gathering of the cellular material and also permits of adjustment for varying leg sizes.

5 Claims, 7 Drawing Figures

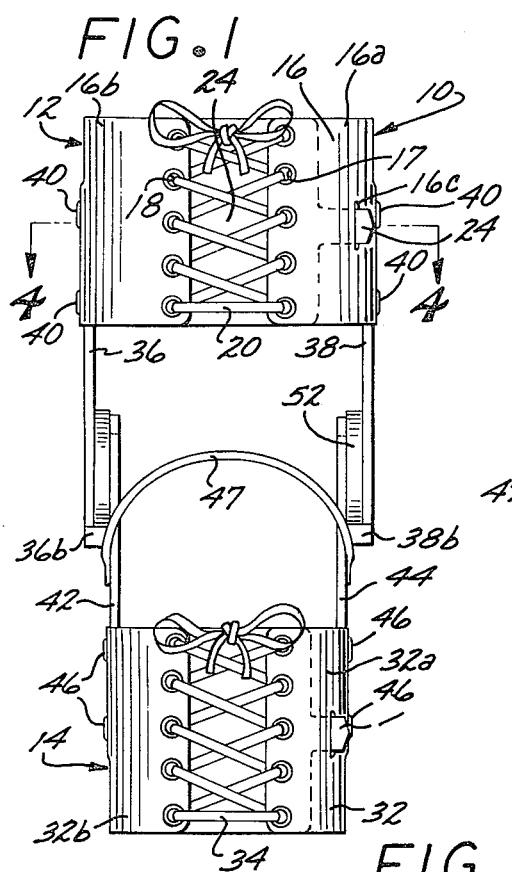
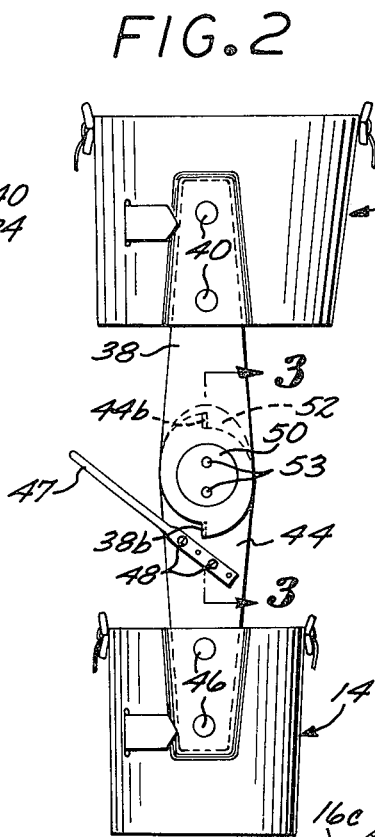
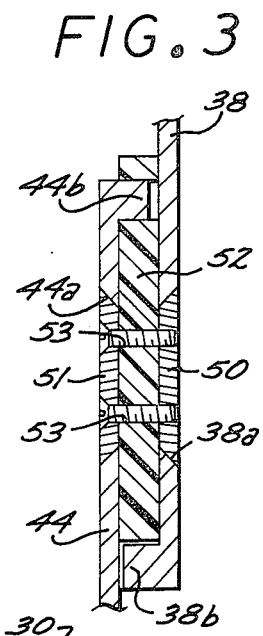
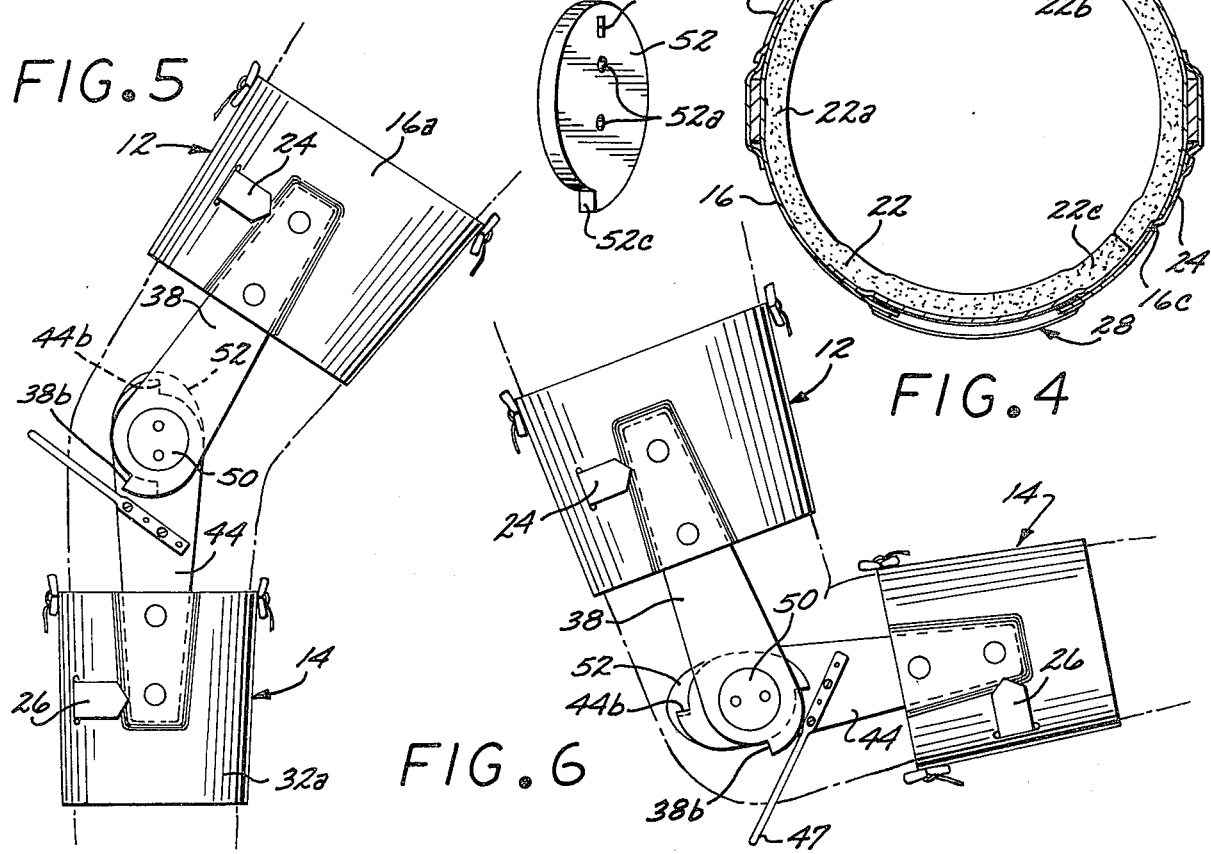

KNEE PROTECTOR AND BRACE

The present invention relates generally to knee protectors and braces, and more particularly to such devices for use in supporting and protecting an athlete's knees during contact and the like.

Athletic endeavors, particularly those participated in by relatively young people, frequently result in knee injuries which persist for many years, if not a lifetime. Contact sports today, such as football, soccer, basketball and the like, are played so enthusiastically tht it is not uncommon for a player to injure his knee such that it thereafter does not withstand pressure and abuse.

For instance, in the sport of football, it is not uncommon for a hard block or tackle to be received by a player either directly against the forward portion of the knee or thigh, or against the side of the leg, either of which tends to force the leg to bend in an unnatural direction. Footwear in such sports have been perfected so as to provide extremely effective traction so that upon receiving a hard or sidewise blow to the leg, the foot does not slip on the turf but rather the full blow or impact goes in the direction of attempting to bend or flex the knee or leg in an unnatural direction.

In view of the foregoing, it is an object of the present invention to provide a knee protector and brace which is capable of affording sufficient rigidity to the knee without in any way impairing its usual mobility.

Another object of the present invention is to provide a knee protector and brace as characterized above having a unique hub affording the normal pivotal action for the knee but wherein there are limit-stops defining the extent of movement of the knee.

A still further object of the present invention is to provide a knee protector and brace as characterized above which comprises a washer which is engaged by various arms to limit the movement of the knee brace so as to prevent unnatural movements of the knee.

An even further object of the present invention is to provide a knee protector and brace as characterized above having thigh and calf members which include soft cellular material which can be straightened against the wearer's leg even though wrapped securely thereagainst.

An even further object of the present invention is to provide a knee protector and brace as characterized above which is simple and inexpensive to manufacture, and which is rugged and dependable in operation.

The novel features which I consider characteristic of my invention are set forth with particularity in the appended claims. The device itself, however, both as to its organization and mode of operation, together with additional objects and advantages thereof, will best be understood from the following description of specific embodiments when read in connection with the accompanying drawings, in which:

FIG. 1 is a front elevational view of a knew protector and brace according to the instant invention;

FIG. 2 is a side elevational view thereof;

FIG. 3 is a fragmentary sectional view taken substantially along line 3—3 of FIG. 2;

FIG. 4 is a transverse sectional view taken substantially along line 4—4 of FIG. 1;

FIG. 5 is a side elevational view showing the knee protector and brace in use;

FIG. 6 is a side elevational view similar to FIG. 5; and

FIG. 7 is a perspective view of one of the washers in the knee protector and brace.

Like reference characters indicate corresponding parts throughout the several views of the drawings.

Referring to FIG. 1 of the drawings, there is shown therein a knee protector and brace 10 according to the present invention. It comprises a thigh member 12 and a calf member 14 which are substantially identical in construction except for the diameter thereof.

The thigh member 12 comprises a pliable member 16 formed of material such as cloth, leather, plastic or the like. Pliable member 16 may be formed in two parts 16a and 16b, each part having a pair of eyelets along each marginal edge thereof. As such, as seen in FIG. 1 of the drawings, the eyelets 17 and eyelets 18 of pliable parts 16a and 16b, respectively, cooperate with a draw string 20 to enable the forward portion of the thigh member 12 to be drawn together. A similar arrangement is provided on the rear of the thigh member 12. This enables the knee brace mechanism to be more effectively centered or positioned on the leg relative to the knee joint, such that either the front or rear lacings can be loosened or tightened, as necessary, to effectuate the proper positioning.

As shown most clearly in FIG. 4 of the drawings, within the pliable material 16 is flexible cellular material 22. As shown, such cellular material may be formed in two parts 22a and 22b with each of such parts protecting the wearer's leg from the lacings 20, both for and aft of the thigh member 12. This prevents injury or chaffing of the wearer's leg.

As shown most clearly in FIGS. 1, 2 and 4 of the drawings, each of such cellular members 22a and 22b is provided with a tab as shown at 24 and 26. The tab 24 is, in fact, secured to end portion 22c of cellular portion 22a so as to extend under the lacing portion 28. In similar fashion the tab 26 is connected to the end portion 22d of cellular member 22b and extends under the lacing portion 30. As shown most clearly in FIGS. 1, 2 and 4 of the drawings, each of the pliable members 16a and 16b is formed with a slot as shown at 16c. Each of the tabs 24 and 26 extends through one of such slots so as to be exposed externally of the thigh member 12 as shown in the drawings.

The calf member 14 is formed similarly to thigh member 12, having a pliable member 32 formed in two parts, 32a and 32b, and lacings 34 in both the front and rear thereof.

A pair of arms 36 and 38 are secured to the thigh member 12 by any appropriate means such as rivets 40 to depending relation on either side of the wearer's knee. In like fashion, a pair of arms 42 and 44 are secured to the calf member 14 by means such as rivets 46 to extend upwadly on either side of such knee.

A U-shaped protector 47 disposed at an angle to the brace itself as shown in the drawings, is secured to the arms 42 and 44 by means of screws or bolts 48. A series of holes are formed in each of the opposite end portions of protector 47 to facilitate adjustment thereof as will hereinafter become apparent.

As shown most clearly in FIG. 3 of the drawings, the arms 38 and 44 are pivotally connected together by a pair of chamfered circular disks 50 and 51 which fit respectively within complementally shaped openings 38a and 44a in arms 38 and 44, a washer 52 and suitable fastening bolts 53.

As shown most clearly in FIGS. 2, 5 and 6 of the drawings, each of the arms 38 and 44 is formed with a limit-stop as shown at 38b and 44b respectively.

Referring to FIG. 7 of the drawings, washer 52 in addition to being formed with a pair of through openings 52a for loosely receiving the bolts or studs 53, is also formed with an opening which may take the form of a slot 52b. In addition thereto, washer 52 is formed with a shoulder 52c.

Referring to FIG. 3 of the drawings, for properly interconnecting the arms 38 and 44, the limit-stop 44b of arm 44 is inserted within slot 52b of washer 52 during assembly. The limit-stop 38b of arm 38 on the other hand, is free to move relative to washer 52 and, as will hereinafter become more apparent, is engageable with the shoulder 52c thereof.

The above arrangement, as shown most clearly in FIGS. 5 and 6 of the drawings, enables the wearer's knee to flex, the washer 52 moving with the arm 44 relative to the arm 38. At that time, the chamfered disk 50 is caused to rotate within the complementally formed opening 38a of arm 38.

Upon the leg receiving a strong blow or force from the front, the subject knee protector and brace will permit the knee to straighten until the limit-stop 38b of arm 38 engages shoulder 52c of washer 52. This is the condition as shown in FIG. 2 of the drawings, and at that time, the brace forcefully prevents any tendency of the knee to be moved in its opposite flexing direction.

The other arms, namely arms 36 and 42, are pivotally connected in the same fashion, being joined by a washer 56 identical in construction to washer 52, and a pair of similar chamfered disks. The washer 56 is connected to arm 42 in the same manner as above-described with respect to washer 52 and arm 44.

To be placed in operation, the thigh member 12 and calf member 14 are strapped or tied to the wearer's leg. At that time, the tabs 24 and 26 are pulled during such tightening operation to insure that the cellular material 22 is straight and smooth against the wearer's leg. Also, such cellular material 22 as well as the tabs 24 and 26 protect the wearer's leg from the lacings 20 and 30.

With the knee protector and brace properly positioned, the U-shaped protector element 47 is always so positioned such that upon the wearer hitting the ground or an object, it is in position to receive the blow. This is shown in FIGS. 5 and 6 where the protector element is in front of the knee when the wearer is standing, and beneath the knee when the wearer is in a falling position. The various holes in the end portions of protector element 47 enable the element to be positioned outwardly or inwardly to accomodate different sizes of legs and knees.

It is thus seen that the present invention provides a knee protector and brace which is easy to affix to the wearer, is comfortable when in proper position, and is effective to not only limit both forward and sidewise blows, but also to limit the amount of adverse twisting or turning of the knee joint.

Although I have shown and described certain specific embodiments of my invention, I am well aware that many modifications thereof are possible.

I claim:

1. A knee protector and brace, comprising in combination, a thigh member adapted to be secured about a person's thigh above the knee, a calf member adapted to be secured about a person's calf below the knee, a pair of arms extending from each of said members toward the knee but on opposite sides thereof, and means forming a pivotal connection between the arms on each side of the knee extending from said thigh and calf member respectively, each of said pivotal connections including a washer between the respective arms, a circular hub inserted within a through opening in one of the said arms and means securing the other of said arms to said washer.

2. A knee protector and brace according to claim 1, wherein each of the arms of each of said pivotal connections is formed with a limit-stop engagable with said washer.

3. A knee protector and brace according to claim 2, wherein said washer is formed with a pair of oppositely facing abutments engagable respectively by said limit-stops on said arms.

4. A knee protector and brace according to claim 3, wherein said washer is free to rotate in either opposite direction on said hub until engaged by said limit-stops of said arms.

5. A knee protector and brace according to claim 4, wherein said means securing said other arm to said washer comprises a slot in said washer engagable by the limit-stop on said other arm and a second circular hub inserted within a through opening in said other arm and fixed to said washer.

* * * * *